United States Patent [19]

Jones et al.

[11] 4,067,935
[45] Jan. 10, 1978

[54] VOLATILE ANESTHETIC VAPORIZING APPARATUS

[75] Inventors: Wilfred Jones, Keighley, England; Keith W. Jones, Lancaster, N.Y.; Travers Fraser Sweatman, Toronto, Canada

[73] Assignee: Cyprane North America, Inc., Tonawanda, N.Y.

[21] Appl. No.: 646,007

[22] Filed: Jan. 2, 1976

[51] Int. Cl.$^2$ .................. B01F 3/04; A61M 15/00
[52] U.S. Cl. .................................. 261/63; 128/188; 137/79; 137/625.31; 261/39 R; 261/64 R; 261/65; 261/107; 261/119 R; 261/DIG. 65
[58] Field of Search ............ 261/39 R, DIG. 65, 101, 261/102, 104, 107, 119 R, 55, 63, 64 R; 128/188, 192–194; 137/79, 625.31

[56] References Cited

U.S. PATENT DOCUMENTS

| | | | |
|---|---|---|---|
| 2,553,446 | 5/1951 | Edmundson et al. | 128/188 |
| 2,911,008 | 11/1959 | Du Bois | 137/625.31 |
| 2,915,061 | 12/1959 | Edmondson et al. | 128/188 |
| 3,192,924 | 7/1965 | Edmundson et al. | 128/188 |
| 3,420,232 | 1/1969 | Bickford | 261/DIG. 65 |
| 3,438,372 | 4/1969 | Sugg et al. | 261/DIG. 65 |
| 3,534,732 | 10/1970 | Bickford | 261/DIG. 65 |
| 3,575,168 | 4/1971 | Jones et al. | 128/188 |
| 3,661,323 | 5/1972 | Farris | 261/39 R X |
| 3,841,560 | 10/1974 | Sielaff | 261/DIG. 65 |
| 3,898,967 | 8/1975 | Bennett et al. | 261/39 R X |

Primary Examiner—Tim R. Miles
Assistant Examiner—Richard L. Chiesa
Attorney, Agent, or Firm—Christel & Bean

[57] ABSTRACT

A volatile anesthetic vaporizing apparatus including a concentration control flow valve means actuated by a substantially linear rotary dial for dividing an inflowing gas stream into two separate streams, one stream being passed over liquid anesthetic to pick up a vapor and the other stream flowing through a bypass duct. The gas stream flowing over liquid anesthetic flows through a temperature responsive valve means, the latter being actuated by a temperature sensitive bimetallic strip which is in direct contact with the vapor saturated air stream which is relatively cool due to the vaporization of the liquid anesthetic. The valve means so situated in the vapor stream essentially does not include any moving parts. Such valve means is formed by the spaced mounting of a planar valve element on a planar surface having vapor opening therein or an inlet passage. The planar valve element has a portion of material removed therefrom and being in contact with a bimetallic strip tends to pivot about the removed portion thereof in response to temperature changes in the vapor saturated stream flow. Such a valve structure avoids problems of sticking, provides substantially laminar flow therethough and automatically compensates for changes in the temperature of vapor saturated air stream as it leaves the vaporizing chamber apparatus once the volumetric anesthetic percentage has been set on the aforesaid rotary dial to maintain such percentage concentration constant over a substantial temperature range.

1 Claim, 10 Drawing Figures

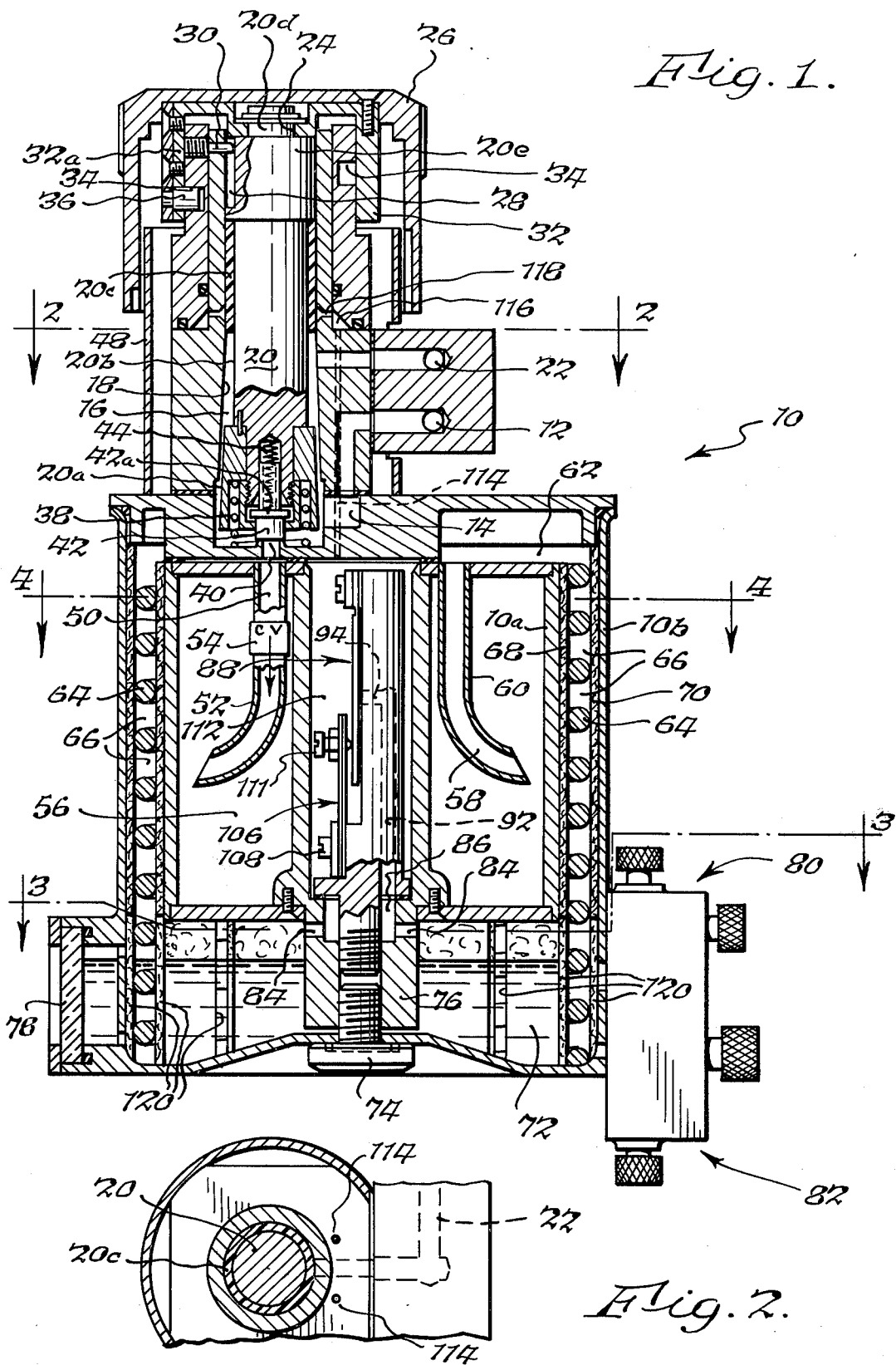

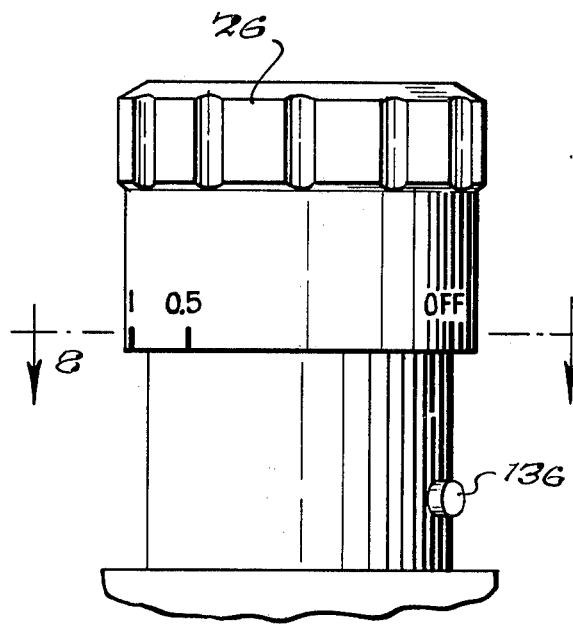
Fig. 7.
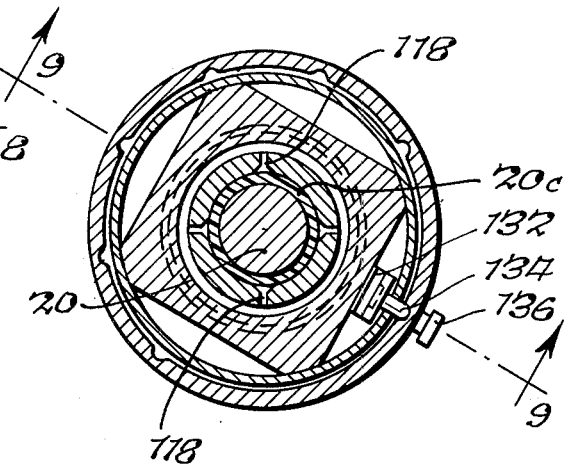
Fig. 8.
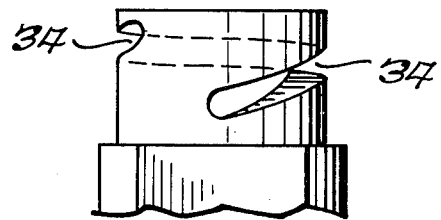
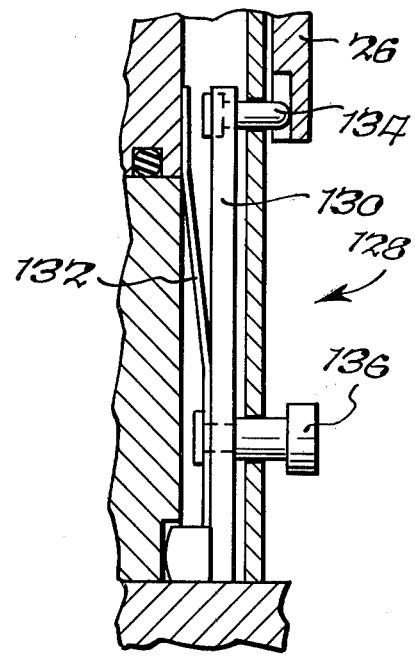
Fig. 9.
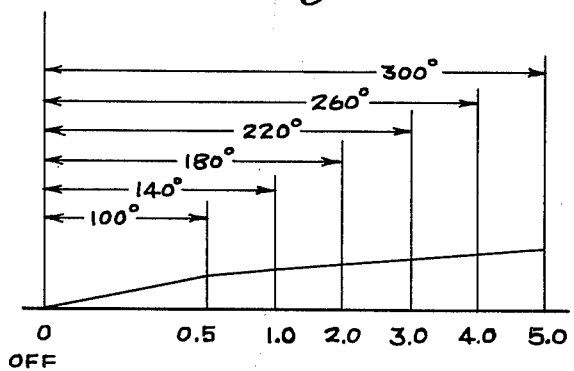
Fig. 10.

VOLATILE ANESTHETIC VAPORIZING APPARATUS

BACKGROUND OF THE INVENTION

This invention relates to an apparatus and a novel thermally responsive control valve associated therewith capable of mixing the vapor of a volatile liquid anesthetic with a gaseous fluid, such as air, oxygen, or nitrous oxide or any other gas or a combination thereof, all of which for convenience are hereinafter included in the term "gas". More specifically, the invention relates to a bypass type of anesthetic vaporizer where the gas input to the vaporizer is divided into two streams which subsequently recombine. In addition, a control valve means is disclosed which includes a rotary dial which operates in a linear manner with respect to changes in anesthetic concentration resulting therefrom.

Most anesthetic vaporizers in use today are designed with a vaporizing chamber and bypass chamber arrangement. Within an inlet portion to such vaporizers the gas flow becomes divided into two separate portions. One portion passes through the vaporizing chamber where it is enriched or saturated with vapor of the liquid anesthetic agent while the other portion completely bypasses such vaporizing chamber. Finally, both of the separate gas flows recombine downstream from the vaporizing chamber and pass through an outlet portion of the vaporizer apparatus. The ratio of the two partial gas flows depends upon the ratio of resistances in the two respective paths or passages, that is the flow resistance in the bypass and the flow resistance in the vaporizing chamber.

The ratio of the resistance in the two gas flow passages can be controlled with the aid of a built-in throttle valve. Changes in the orifice of the valve alter the distribution of the main gas inflow, which in turn, alters the concentration of volatile anesthetic in the gas leaving the vaporizer.

A number of problems have been encountered in the design of anesthetic vaporizers which in large part are related to the safety requirements of such devices. In general it is most desirable for this reason that a user of an anesthetic vaporizer be able to specify a particular output flow having a particular anesthetic concentration under a variety of operating conditions and any factor detracting from this type of performance may be viewed as a problem associated with any particular vaporizer structure.

One such potential problem results if the portion of gas passing through the vaporizing chamber does not become fully saturated. The resultant effect is that the output concentration decreases as flow through the unit increases and accordingly such concentration could be at variance with that indicated by the settings on the apparatus. In addition, a most important feature of a vaporizer is that its output performance should be independent of ambient temperature, such temperature being reflected in the temperature in the input gas to the unit. This aspect of vaporizer design involves the fact that varying amounts of anesthetic vapor may be absorbed by input gases at different temperatures, generally input gases at higher ambient temperatures being capable of absorbing more anesthetic vapor. The simple solution to attaining an output performance which is independent of ambient temperature would be to keep the vaporizer at a constant temperature in an attempt to maintain gas flow through the unit at a controlled temperature to thereby control vaporization of an anesthetic in a knowledgeable manner. However, such a method would incorporate the additional problems of a temperature control system for the vaporizer and the potential malfunction of the component parts thereof which would in turn affect the performance of the vaporizer.

Another problem presented with the design of an accurate vaporizer apparatus concerns the heat loss in the liquid anesthetic due to the heat needed for vaporization thereof which is taken from the liquid anesthetic itself in the vaporizing chamber which results in a decrease in temperature therein and in a corresponding decrease in vapor pressure. This results potentially in a decrease in the delivered concentration of the vaporizer flow. Accordingly, it is most desirable that the alteration of the gas flow through the vaporizing chamber be readily adjusted in an automatic manner since temperature decreases resulting from vaporization can be quite rapid.

SUMMARY OF THE INVENTION

Accordingly, one object of the present invention is to provide a new and improved vaporizer apparatus including a thermally responsive valve activated by a bimetallic strip which is placed in the outlet of the vaporization chamber so as to quickly respond to temperature changes therein to accordingly adjust the gas flow therethrough.

Another object of the present invention is to provide a vaporizer structure wherein all of the gas passing through the vaporizing chamber continuously reaches saturation so as to insure proper concentration of the output gas flow.

A further object of the present invention is to provide the aforesaid vaporizer with a thermally responsive flow control valve in the outlet of the vaporizing chamber which insures that the concentration of the total gas outflow of the apparatus is constant and independent of the ambient temperature.

Still another object of the present invention is to provide a thermally responsive flow control valve in the outlet of the vaporizing chamber as described hereinabove which is relatively simple in design, includes no pivot connections and accordingly is more reliable in service in view of a minimum number of moving parts so arranged that function is elevated while still providing for laminar low therethrough.

In summary, the present invention provides an anesthetic vaporizer and a thermally responsive flow control valve in the outlet of a vaporizing chamber thereof which is unique in construction and provides highly desirable operational characteristics to the apparatus. The valve in the outlet of the vaporizing chamber includes a housing having a planar surface portion and a valve inlet passage opening into the planar surface portion with all of the flow through the chamber passing through the inlet passage. In addition, a planar valve element is affixed to the planar surface in a spaced manner by means of a shim element and includes a grooved portion about which the planar valve element bends toward and away from the inlet passage to variably restrict the outflow of gas from the vaporizing chamber. Due to the planar form of the aforesaid parallel surfaces, laminar flow results with respect to the gas flow passing therebetween. A thermally responsive bimetallic strip abuts the planar valve element and determines its disposition with respect to its spacing from the planar surface of the valve housing. In this manner temperature changes in the vaporizing chamber are reflected in the bimetallic strip which adjusts the spacing of the valve element.

In addition, to the aforesaid valve structure in the outlet of the vaporizing chamber, an axially operated, tapered valve is employed to control the flow of gas through a bypass chamber of the vaporizer for varying the anesthetic concentration of the resultant flow of gas through the main outlet of the vaporizer. The latter valve means is actuated by a percentage control dial which is coupled to a pin for engaging a spiral groove in the sidewall of the valve assembly. The spiral groove has a variable pitch along its axial length so as to variably move the valve in an axial sense at different rotational positions of the aforesaid dial in view of the fact that gas flow through the tapered valve structure is not proportionate to changes in the axial disposition of such valve. Accordingly, the variable pitch of the aforesaid groove is designed to offset or compensate for the non-linear characteristic of the tapered valve with respect to axial movement thereof and corresponding gas flow therethrough so that the concentration of the output flow from the vaporizer is varied in a linear manner with respect to rotation of the percentage control dial.

The foregoing and other objects, advantages, and characterizing features of the present invention will become clearly apparent from the ensuing detailed description of an illustrative embodiment thereof taken together with the accompanying drawings wherein like reference characters denote like parts throughout the various views.

BRIEF DESCRIPTION OF THE DRAWINGS

FIG. 1 is a side elevational view in section of the improved vaporizer constituting the present invention;

FIG. 2 is a top view partly in section of the valve means controlling the flow of gas into the bypass chamber of the apparatus as taken about on line 2—2 of FIG. 1;

FIG. 7 is a perspective view of the rotary percentage dial for controlling the percentage of concentration of anesthetic vapor in the outflow gas of the vaporizer considered herein;

FIG. 8 is a top view of the mechanism shown in FIG. 7 as taken about on line 8—8 therein;

FIG. 9 is a fragmentary detailed illustration in vertical section of a locking means utilized to secure to dial shown in FIG. 7 in an "off" position as taken about on line 9—9 of FIG. 8;

FIG. 10 shows a fragmentary portion of the valve stem employed to axially adjust the bypass valve of the vaporizer and which includes a helical groove for mating engagement within the rotary dial shown in FIG. 7.

FIG. 10 further includes a diagrammatic representation of the bypass valve operation as a function of rotation of the dial shown in FIG. 7.

DETAILED DESCRIPTION OF A PREFERRED EMBODIMENT

Figure 3:
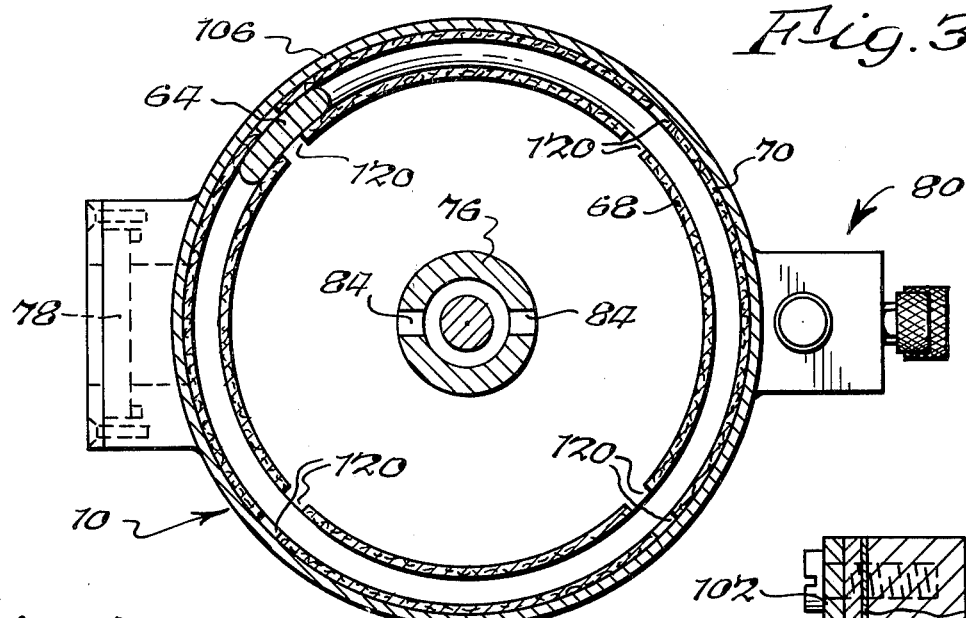
FIG. 3 is a top view of the vaporizing chamber in section as taken about on line 3—3 of FIG. 1.
Figure 4:
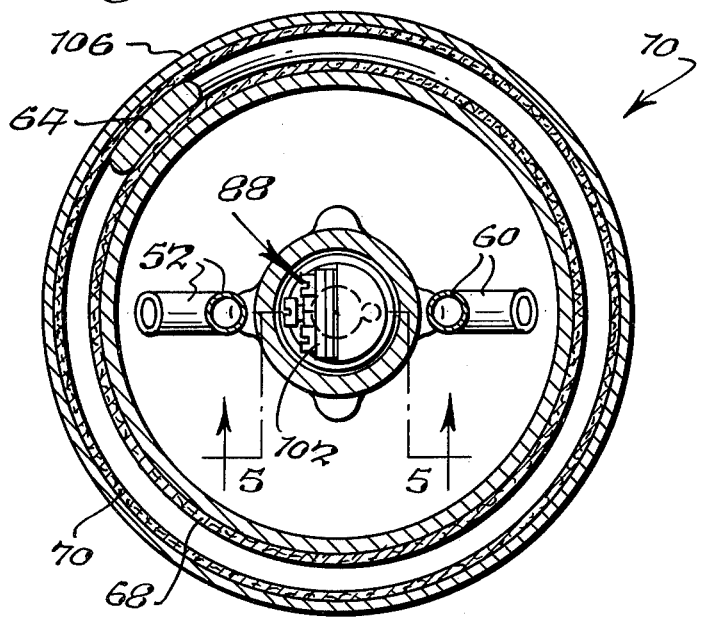
FIG. 4 is a top view in section of the upper portion of the vaporizing chamber in which the valve means controlling flow through the vaporizing chamber is located as taken about on line 4—4 of FIG. 1.
Figure 6:
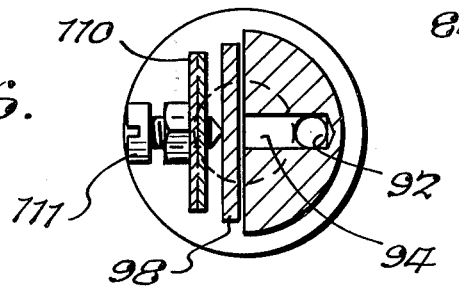
FIG. 6 is a detailed top view partly in section of the inlet passage of the aforesaid vaporizing chamber valve as taken about on line 6—6 of FIG. 5.

Referring now in detail to the illustrative embodiment depicted in the accompanying drawings there is shown in FIG. 1 a vaporizer having a casing 10 formed of a plurality of component parts which assume the configuration shown and to be described in more detail hereinbelow. A gas or air inlet port 12 is provided to communicate inwordly and downwardly within the sidewalls or housing of the apparatus through chamber 14. Chamber 14 opens into and upwardly extending bypass chamber 16 which is defined between the inner sidewall 18 of the housing and the lower portion of the bypass valve assembly generally indicated as 20. The lower portion of the bypass valve means 20a is tapered upwardly as is the inner sidewall 18 adjacent thereto. As will be more fully apparent, as the valve portion 20a is raised, the bypass opening 16 becomes more restricted thereby restricting the amount of gas flowing inwardly through chamber 14 which may flow upwardly and directly out through the vaporizer outlet 22.

The upper portion or spindle 20b of the bypass valve is provided with a Teflon sleeve 20c which is adapted to vertically slide in the upper portion of sidewall 18, the latter being non-tapered to cooperatively fit with sleeve 20c. The extreme upper end of bypass valve 20 includes an annular groove 20d for cooperative engagement with protrusions 24 depending from the undersurface of a rotary dial or actuator 26 which is provided to adjust the axial disposition of valve portion 20a within the bypass chamber 16.

A collar portion 20e below groove 20d includes a vertically oriented groove 28 which receives a key 30 protruding from the upper end of sidewall 18. The key 30 operates to prevent the valve assembly 20 from rotating during the axial movement thereof as controlled by actuator dial 26. The actuator 26 further includes a downwardly depending portion 32 which skirts the upper portion of housing 10. As will be described in more detail hereinbelow, the outer sidewall of the upper portion of housing 10 includes a spiral groove 34 of varying pitch which receives a pin assembly 36 protruding inwardly from the generally skirted portion 32 of cap 26. As shown, the skirted portion 32a is adapted for the mounting of pin 36. The lower portion 20a of bypass valve 20 further includes an internal annular bore form mounting of spring 38 which tends to urge the bypass valve assembly upwardly. However, due to the retention of protrusions 24 in groove 20d of the valve member and the engagement of pin 36 within the spiral groove 34 in the housing sidewall, the valve assembly 20 may only rise when permitted by the positioning of pin 36 within various elevated positions in spiral groove 34.

The upper portion of the vaporizer is surrounded by a circumferential shield portion 48 which is in turn overlapped by the outer skirt portion of cap 26 so as to present a clean appearance to the structure.

In addition to the above, the lower end portion of valve assembly 20 partially defines a passage leading from chamber 14 to a valve seat 40. Valve seat 40 defines an inlet opening to a vaporizing chamber wherein liquid anesthetic is evaporated into the air flow stream passing through the valve seat 40. The lower end of valve assembly 20 further includes a valve element 42 which is spring biased downwardly with respect to the valve assembly 20 by spring 44 housed within assembly 20. The valve element 42 includes a flanged portion 42a which is provided to abut the underlying edge of valve assembly portion 20a within which valve element 42 is mounted upon sufficient movement of the assembly 20 away from valve seat 40.

Valve seat 40 leads to the vaporizing chamber through the following paths. Valve seat 40 opens to passage 50 defined within tude 52 which leads to a one way check valve 54. Check valve 54 opens to an annular chamber 56 which in turn feeds into passage 58 defined within tube 60. Passage 58 proceeds upwardly and opens into chamber 62 from which subsequent flow of gas becomes subjected to vaporization of anesthetic.

Chamber 62 opens into a spiral path defined between adjacent coils of a helical rod 64. The vertically separated passages 66 are further defined by the housing sidewalls 10a and 10b which have liquid absorbent wicks 68 and 70 disposed thereon and which extend downwardly into sump area 72 which is at least partially filled with liquid anesthetic. The bottom portion of the vaporizer housing 10b is maintained in place with respect to the upper housing portion by means of a bolt 74 which is engaged with a downwardly depending internal portion of the housing 76.

Figure 5:
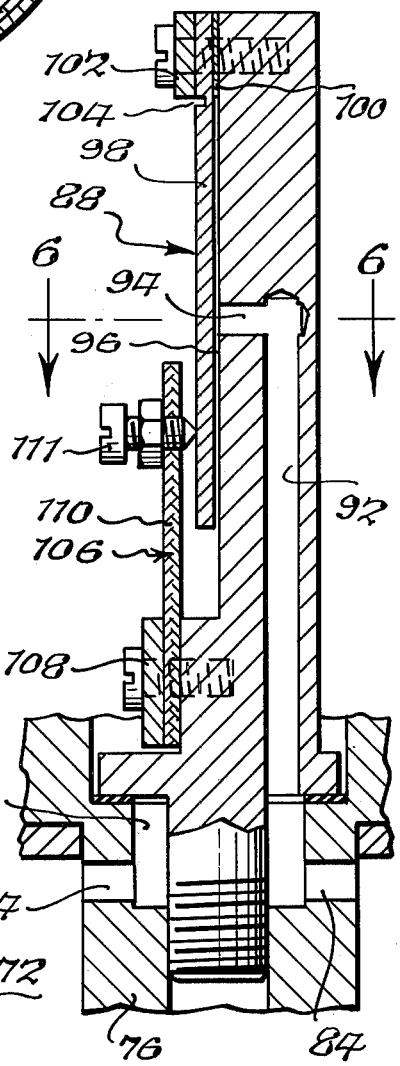
FIG. 5 is a vertical view partly in section illustrating the valve means disposed in the vaporizing chamber as taken about on line 5—5 of FIG. 4.

There is an observation window 78 through the base portion of the housing for observing the level of the liquid anesthetic within the sump area 72. The vaporizer casing is further provided in its lower right hand portion as seen in FIG. 1 with a filler port 80 for the entry of liquid anesthetic into sump 72 and an associated drainage port 82 for draining liquid anesthetic from the housing of sump area 72 when desired. As air leaving passage 62 flows downwardly along the helical passages 66, it becomes fully saturated with liquid anesthetic maintained in wick 68 and 70 and as the gas-anesthetic vapor flow reaches the surface of the liquid in sump 72, it flows laterally into passages 84 in element 76 and upwardly into the inlet passage 86 of the thermally responsive flow control valve generally indicated as 88 and shown in detail in FIG. 5.

The flow through ports 84 goes through chamber 86 upwardly through the vertical passage 92 to the horizontal passage 94 to open into a planar surface 96 of the valve housing. A planar valve element 98 is mounted in a pivoted manner on the planar surface 96 in a spaced, substantially parallel relationship with respect to surface 96. Valve element 98 is spaced from surface 96 by means of an intermediate shim means 100 and the valve element 98 and shim 100 are held in a mounted position by a bolt assembly 102. With the provision of a groove 104 in the surface of the valve element adjacent to its pivot point on shim 100, valve 98 may be more easily pivoted toward and away from the planar surface 96 to varibly restrict the gas-anesthetic vapor mixture flowing outwardly in a laminar manner between the planar surface 96 and the planar valve element 98. In this regard a temperature responsive element 106 is affixed to the housing of valve 88 by means of a bolt assembly 108 to engage planar valve member 98. As is apparent from FIG. 5 and easily understood by one skilled in the art, the strip 110 is of bimetallic nature and includes a bolt means 111 to adjustably control the pivoting of the planar valve element 98 in response to temperature changes reflected in the temperature of the housing of the control valve 88. As will be described hereinbelow, bimetallic strip 110 senses such temperature changes so that the valve 98 is automatically adjusted to vary the pressure drop of gas flow through the container for liquid anesthetic so as to maintain the anesthetic concentration of gas delivered from the vaporizer apparatus substantially constant over a range of temperature conditions.

Returning now to FIG. 1 the gas-vapor flow issuing from control valve 88 flows into chamber 112 and upwardly therefrom through a pair of vertical passageways 114 shown in top view in FIG. 2. The vertical passageways 114 connect with a circumferentially extending passageway 116 which in turn feeds a plurality of ports 118 which extend radially inwardly from channel 116. The ports 118 are effectively blocked by the Teflon sleeve 20c forming part of the valve assembly 20 when the latter is in a relatively lowered condition which also results in the valve 42 engaging the valve seat 40.

In operation, the inlet port 12 of the apparatus is connected, for example, to an appropriate source of fresh gas. The quantity flow of such fresh gas is determined independently of the instant apparatus but such flow could be for example in the range of 0.5 to 10.0 liters of fresh gas per minute. The fresh gas passes through inlet 12 to chamber 14 wherein the flow divides, one stream flowing downwardly through valve seat 40 into passage 50 while a second stream flows upwardly into bypass chamber 16 into the outlet port 22 and chamber associated herewith. As shown in FIG. 1, the apparatus is in an "off" position, however, as determined by the vertical positioning of the valve assembly 20 by the actuating cap 26. As shown, the cap 26 has been closed down in a clockwise direction if viewed from the top with the drive pin 36 urging the valve assembly 20 downwardly against the upward bias of spring 38 disposed against the bottom of valve 20. During the rotation of cap 26, the pinoor key 30 prevents the valve assembly 20 from rotating while the Teflon sleeve 20c vertically slides within the housing of the apparatus. Accordingly, relative rotation exists between cap 26 and the assembly 20 by means of the protrusions 24 and groove 20d forming part of the assembly 20. In the closed position shown in FIG. 1, the Teflon sleeve 20c overlaps the ports 118 which communicate with the vaporizing chamber so as to preclude any possibility of anesthetic vapor issuing therefrom should air be passed through the bypass chamber 16. Similarly, with cap 26 in the "off"position and sleeve 20c overlapping ports 118, the spring loaded valve 42 is affirmatively biased to engage valve seat 40 so that any air passing inwardly through port 12 may not pass to the vaporizing chamber and must entirely flow through the bypass chamber 16 and out port 22.

When the vaporizer is to be used, the cap 26 is rotated in a counterclockwise direction so that the pin 36 moves upwardly in groove 34 allowing spring 38 to urge the valve assembly 20 upwardly. Of course, it would be obvious to one skilled in the art that the cap 26 could be assembled so as to rotate clockwise in order to operate the vaporizer and that potentially groove 34 could be incorporated into cap 26 which would engage a stationary pin equivalent to 36 on the housing of the unit. In any event, as the valve assembly 20 rises, the flange 42a on valve 40 engages the underlying edge of bypass valve portion 20a so that the bias of spring 44 is restrained and valve 42 is positively lifted upwardly from valve seat 42. Upon lifting of valve 42, a stream of inflow gas from chamber 14 will pass downwardly through passage 50 through checkvalve 54 and a second stream of inflow gas will pass upwardly through bypass passage 16 to recombine with vapor saturated gas flow passing from ports 118, the latter being opened as sleeve 20c rises with the assembly 20. The flow of the bypass stream and the streams issuing from ports 118 mix and the resultant flow of specified anesthetic percentage flows outwardly through port 22.

It has been found that the potential sticking of the main spindle portion of valve assembly 20 has been eliminated by the provision of the Teflon bearing sleeve 20c. Such a potential problem of sticking is mainly due to deposits of Thymol which is added to Fluothane as a stabilizing agent, all of which is contemplated for use in the present vaporizer. Generally, the valve 42 in the base of the spindle of the assembly 20 is Teflon faced and accordingly resists sticking, although the latter feature is not really necessary due to the positive lift provided by flange 42a.

As the valve assembly 20 rises, the bypass passage 16 becomes more restricted so that more of the inflow gas flows downwardly through passage 50 which, as will be described, results in more of the inflow gas eventually issuing from ports 118 fully saturated with anesthetic vapor for recombining with the bypass flow through area 16 prior to passage to outlet port 22.

It is to be further understood that the tapered portion 20a bypass valve assembly 20 is so adjusted that it never engages the adjacent tapered sidewall 18. There is therefore always a gap so that a jamming of valve portion 20a cannot result.

As stated, the stream of inflow gas circulating through the vaporizing chamber passes through passage 50, pas check valve 54 into annular chamber 56. The flow continues upwardly through conduit 60 and passage 58 therein to chamber 62. From chamber 62, the air flow passes downwardly along the spiral passages 66 defined by the tubes 64 and the adjacent wicks 68 and 70. As the air flow so passes, it becomes fully saturated with vapor issuing from the aforesaid wicks, the bottoms of which extend into the liquid pool of anesthetic 72. As seen in FIGS. 1 and 3, the inner wick 68 includes bifurcated portions 120 so that as the air flow through the vaporizing chamber approaches the surface of the liquid anesthetic, it passes laterally thereover to enter ports 84 and then upwardly through inlet passage 92 of the thermally responsive flow control valve 88. From passage 92, the saturated vapor passes laterally outward beneath the adjusted spacing of planar valve element 98 in a laminar manner and enters chamber 112 so as to subsequently flow upwardly through internal passages 114 to chamber 116 and radially through ports 118 to recombine with the bypass flow of input gas passing through area 16.

One of the features of this apparatus is the fact that the flow control valve 88 is directly responsive, in a thermal sense, to the temperature of the air flow through the vaporizing chamber since the bimetallic strip 106 is in intimate contact with the flow path thereof. Accordingly, one may rotate dial 26 in a counterclockwise direction as shown in FIG. 7 to specify a certain percentage by volume of vaporized anesthetic in the air flow. Such a setting will lift valve assembly 20 to a predetermined position which, under standard operating conditions with respect to flow control valve 88, will result in an outflow concentration as specified. In other words, under standard operating conditions with respect to flow control valve 88, the percentage of input flow through chamber 14 passing to the vaporizing chamber will be dependent upon the position of valve assembly 20, valve 88 having a prescribed opening for such standard conditions. Once such a concentration has been called for by the setting of cap 26, the bimetallic strip 106 of flow control valve 88 senses the temperature of the saturated vapor leaving the vaporizing container or chamber so as to make adjustments for the temperature not corresponding to the reference temperature or standard operating temperature referred to hereinabove for such valve.

Accordingly, as the temperature of the input gas to the vaporizing chamber decreases as a result of ambient conditions or as a result of the vaporization process itself, and the capacity of the relatively lower temperature gas in the vaporizing chamber for absorbing anesthetic vapor decreases, additional input gas from chamber 14 is diverted to the vaporizing chamber to compensate for the aforesaid reduced vapor capacity due to the lowered temperature whereby the resultant mixture appearing in part 22 will remain constant for different ambient temperatures in which the unit is used and for different temperatures within the vaporizing container portion of the unit. Therefore, upon such a decrease in temperature, the bimetallic strip 106 will bend slightly to the left allowing the planar valve element 98 to spring slightly to the left to thereby reduce the pressure drop across valve 88 resulting in more flow through the vaporizing chamber. Conversely, upon sensing temperatures in excess of a reference temperature the bimetallic strip 106 will bend to the right tending to close down valve 88 thereby increasing the pressure drop thereacross and restricting flow of air through the vaporizing chamber which at higher temperatures would have a higher capacity for absorbing anesthetic vapor.

Accordingly, it is to be understood that the setting for the resultant air flow issuing from port 22 is set by means of rotating cap 26. This results in a fixed mechanical positioning of the spindle in valve assembly 20. Compensation for the various temperatures experienced in the environment in which the vaporizer is used and in flow temperatures resulting in the unit itself are provided by flow control valve 88 in an automatic manner so that the mixture in port 22 remains constant.

Another feature of the present invention resides in the nature of the variable pitch of groove 34 which is engaged by pin 36. As stated hereinabove, the pressure drop across bypass passage 16 is not linearly proportionate to the axial movement of valve assembly 20. Accordingly, the groove 34 includes a variable pitch so that valve assembly 20 will vertically move in various amounts for equal degrees of rotation of cap 26. However, as illustrated in the graph of FIG. 10, such disproportionate axial movements of assembly 20 can be designed to result in proportionate changes in outflow concentration for proportionate degrees of rotation of cap 26. As shown in FIGS. 7 and 10, the movements between 0.5% and 1% is not proportional to the subsequent 40° movements of cap 26 since the 0.5% is provided on the unit only as a minimum percentage setting. Obviously, the feature of having the concentration related to proportional degrees of rotation of cap 26 is highly desirable. In addition, cap 26 is provided with a positive locking feature generally indicated at 128 in FIG. 9. The lock 128 includes a cantilevered portion 130 with a spring portion 132 attached to the backside thereof for biasing portion 130 outwardly so that a pin 134 on the free end of portion 130 engages a recess in the skirted portion of cap 26. In this manner, the cap 26 may not accidentally be opened until the button means 136 is urged inwardly to release pin 134 from the recess in the skirt of cap 26 so that the latter may be operated. Furthermore, upon rotation of cap 26, the depressed pin 134 "clicks" in notches on the inner surface of the skirt of cap 26 which are aligned with the cap settings so that a setting could potentially be made by sound or touch sensitivity alone as for example if no light were available.

Another feature of the present invention is that in which liquid anesthetic in the bottom portion thereof may not accidentally enter the bypass stream 16. Since it is anticipated that vaporizers may be easily removed for a variety or reasons, with the possibility of them being laid on their side or inverted when charged with liquid anesthetic, a nonspillable sump with respect to the bypass passage becomes highly desirable. In regard to tubes 52 and 60, should liquid anesthetic flow upwardly through the passages 66, for instance when the unit is inverted for one reason or another, such liquid would flow into chamber 62 and partially up tube 60. However when the unit is placed right side up only a small portion of the liquid would flow downwardly through tube 60 and fall to the bottom of chamber 56. In addition, the placement of check valve 54 insures that no liquid could flow up passage 50.

From the foregoing, it is apparent that the objects of the present invention have been fully accomplished. As a result of the instant invention an improved anesthetic vaporizer is provided for maintaining the uniformity of the concentration of anesthetic in a gas flow so that the vaporizer may be used in a reliable and compentent manner.

Having thus described and illustrated a preferred embodiment of the invention, it will be understood that such description and illustration is by way of example only and that such modifications and changes as may suggest themselves to those skilled in the art are intended to fall within the scope of the present invention as limited only by the appended claims.

We claim:

1. Vaporizing apparatus for a volatile anesthetic including:

a body forming a container for liquid anesthetic wherein such liquid can be vaporized by the flow thereby of a gas, said container having a gas inlet thereto and a gas-anesthetic vapor outlet therefrom, a bypass chamber for gas not passing through said container and a main inlet to and a main outlet from said bypass chamber, passage means connecting said main inlet to said container gas inlet, passage means connecting said container gas-anesthetic vapor outlet to said main outlet of said bypass chamber from mixing of gas-anesthetic vapor with gas passing through said bypass chamber, valve means for selectively controlling the relative flow of gas into said bypass chamber and said container so as to vary the anesthetic concentration of the recombined, mixed flow through said main outlet of said bypass chamber which passes outwardly from the vaporizing apparatus, said valve means comprising:

an elongated valve element disposed within said main inlet to said bypass chamber and being axially movable therein and said valve element and surrounding wall surface of said main inlet being so formed that an opening is defined therebetween, said opening varying in cross-section in a non-linear manner with respect to corresponding axial movement of said valve element, a rotatable valve element actuator in operable connection with said valve element for adjusting the axial position of said valve element within said main inlet whereby gas flow through said main inlet to said bypass chamber and to said container can be varied to vary the anesthetic concentration of the recombined, mixed flow through said main outlet, and connection means rotatably connecting said actuator to said valve element for adjusting the axial position of the latter, whereby the size of said valve element opening and the gas flow associated therewith are linearly proportional to the operable rotational movements of said actuator, said connection means including a spiral groove of varying, non-linear pitch and drive means on said actuator engaging said groove to effect movement of said valve element upon rotation of said actuator wherein said non-linear pitch of said groove offsets the non-linear nature of said valve element opening so that gas flow through said bypass chamber and the anesthetic concentration of the recombined, mixed flow through said main outlet varies linearly and uniformly with respect to proportionate degrees of rotation of said actuator over substantially the entire operational range of said actuator.

* * * * *